United States Patent
Döring

(12) 
(10) Patent No.: US 6,429,426 B1
(45) Date of Patent: Aug. 6, 2002

(54) IONIZATION CHAMBER WITH ELECTRON SOURCE

(75) Inventor: Hans-Rüdiger Döring, Leipzig (DE)

(73) Assignee: Bruker Saxonia Analytik GmbH, Leipzig (DE)

( * ) Notice: Subject to any disclaimer, the term of this patent is extended or adjusted under 35 U.S.C. 154(b) by 24 days.

(21) Appl. No.: 09/617,716

(22) Filed: Jul. 17, 2000

(30) Foreign Application Priority Data

Jul. 17, 1999 (DE) .......................................... 199 33 650

(51) Int. Cl.[7] ................................................. H01J 49/00
(52) U.S. Cl. ..................... 250/288; 250/286; 250/423 R
(58) Field of Search .......................... 250/423 P, 423 F, 250/423 R, 424, 435, 288, 286, 287, 281, 282

(56) References Cited

U.S. PATENT DOCUMENTS

| | | |
|---|---|---|
| 3,881,111 A | 4/1975 | Stephens et al. |
| 4,218,617 A * | 8/1980 | Cazaux ....................... 250/305 |
| 4,382,181 A * | 5/1983 | Wang ........................ 250/305 |
| 5,021,654 A | 6/1991 | Campbell et al. |
| 5,528,150 A | 6/1996 | Stearns et al. |
| 5,563,411 A * | 10/1996 | Kawata et al. .............. 250/306 |
| 5,969,349 A * | 10/1999 | Budovich et al. ........... 250/286 |

FOREIGN PATENT DOCUMENTS

| | | |
|---|---|---|
| DE | 196 27 620 | 11/1997 |
| DE | 196 27 621 | 1/1998 |
| WO | 93/22033 | 11/1993 |

OTHER PUBLICATIONS

P. Begley et al., Photoemissive Ionisation Source for Ion Mobility Detectors; Journal of Chromatography, 588 (1991); pp. 239–249.

* cited by examiner

Primary Examiner—Kiet T. Nguyen

(57) ABSTRACT

Ionization chamber, especially for an ion mobility spectrometer, with a non-radioactive electron source. The chamber consists of two compartments, of which one is evacuated and contains an electron source, and the other represents the reaction chamber of the IMS. In the evacuated compartment, X-ray quanta are produced in an anode by electron bombardment and these X-ray quanta can penetrate a partition between the two compartments. The partition between the two compartments is impermeable to electrons from the source and to gas molecules. In one or several conversion layers within the reaction compartment, X-ray quanta are converted to quanta of a lower energy and/or photoelectrons that can ionize the air constituents at a high level of efficiency.

43 Claims, 2 Drawing Sheets

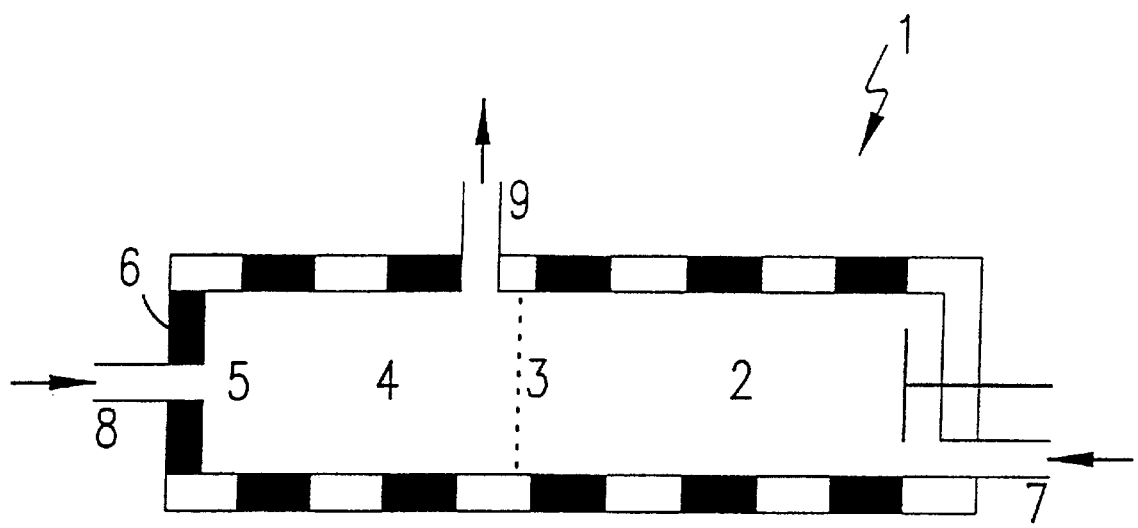
Fig.1 - PRIOR ART
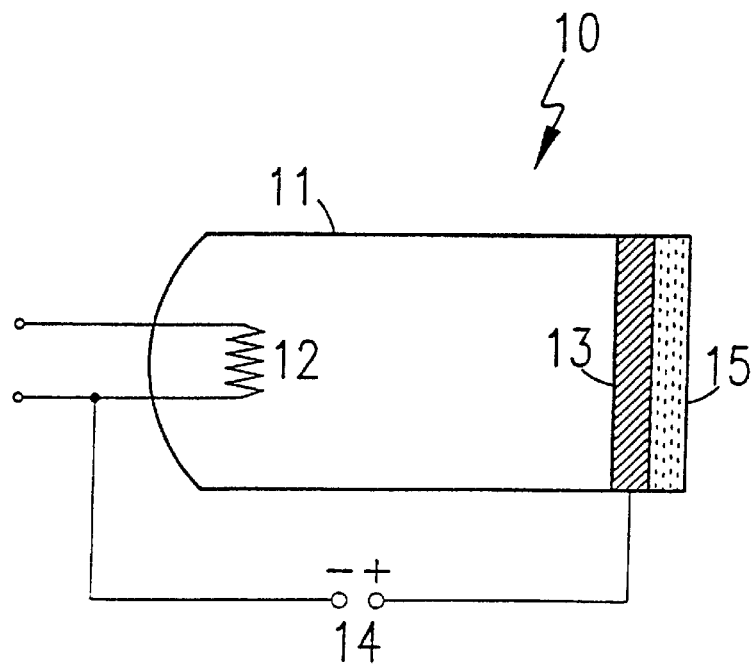
Fig.2

IONIZATION CHAMBER WITH ELECTRON SOURCE

BACKGROUND OF THE INVENTION

The present invention relates to an ionization chamber with a non-radioactive ionization source, preferably of an ion mobility spectrometer, an electron capture detector, or a mass spectrometer with ionization at atmospheric pressure (APIMS), with a reaction compartment, a supply line to feed analyte into the reaction compartment, and a discharge line to remove the analyte, whereby the reaction compartment is separated from an evacuated compartment by a partition which is impervious to gas, whereby a non-radioactive electron source is installed in the evacuated compartment, and forms the negative pole of an acceleration section.

Such an ionization chamber is known from U.S. Pat. No. 5,969,349 for an ion mobility spectrometer (IMS) and from U.S. Pat. No. 6,023,169 for an electron capture detector (ECD).

Ion mobility spectrometers (IMS) were introduced in the early 1970s in order to analyze and detect organic vapors in air. An ion mobility spectrometer consists of the reaction chamber in order to generate ions of substances to be analyzed, and a drift chamber in order to separate the ions. In the reaction chamber radioactive materials are normally used to generate the ions to be analyzed, e.g. tritium, $^{63}Ni$, $^{241}Am$ etc. The disadvantage of such an IMS is that the use of a radioactive ionization source can be hazardous for the environment and the health of the maintenance personnel.

In this connection a large number of attempts were made to design IMS setups with non-radioactive ionization sources in the reaction chamber, e.g. photo-emitters for the generation of electrons. However, in these experiments it was not possible to rule out contact between analyzed gas molecules and the surface of the source. This is one of the reasons for instability in detector displays because such contact can alter the operating characteristics of a non-radioactive source.

Known IMS setups consist of a reaction chamber, a drift chamber, a non-radioactive electron source which is integrated into the said reaction chamber, a supply line connected to the reaction chamber in order to feed an analyte, and a discharge line to remove the analyte, as well as a capture electrode integrated into the drift chamber (for example, see Begley P., Carbin R., Fougler B. F., Sammonds P. G., J. Chromatogr. 588 (1991) Page 239).

The disadvantage of this known IMS is that the analyte makes direct contact with the surface of the non-radioactive ionization source, which in turn alters the operating conditions of the said ionization source and can be one of the reasons for instabilities in detector display.

U.S. Pat. No. 5,021,654 describes how a radioactive ion source can be simply replaced by a non-radioactive one in the form of a thermionic emission source.

With the ionization chamber referred to at the beginning it is possible to create an IMS or ECD setup which avoids contacts between the analyte and the ionization source and permits operation with positive and negative ions.

Due to the fact that the electron source is accommodated in a separate, evacuated compartment, all contact between the gas and its surface is avoided and prevailing operating conditions are always uniform and controlled. On the other hand, the transparency of the partition for electrons makes it possible for them to pass into the second compartment of the reaction chamber, which forms part of the IMS gas circuit and where, after the electrons have entered through the partition, molecule ions are formed for positive or negative IMS operating modes, by means of reactions with the gas molecules. In a preferred embodiment the partition which divides the reaction chamber into two compartments is made from mica. This is a particularly suitable material both with a high level of electron transparency and sufficient imperviousness to gas. To avoid any bending in the partition due to differences in pressure, it should preferably be supported by a metal mesh, e.g. made from copper, with minimal scatter and absorption of electrons.

Although the known reaction compartment already solves a range of problems, there is still the serious problem that, for the partition to be adequately transparent for electrons it must be extremely thin. This involves the risk that despite the supporting measures mentioned the window may mechanically break or leak due to the difference in pressure, particularly in light of the additional load exerted by the intensive electron bombardment, which, among other things, leads to a local thermal load which can only be dissipated inadequately via the supporting mesh and an extremely thin metal film. Most of the electrons hitting the partition are still absorbed in the wall and as operation of the electron source progresses they cause irreversible changes to the partition, as a result of which its imperviousness is reduced. Only electrons in the sub-ppm range can penetrate the wall and ionize the air components in the reaction compartment, which is why only small measuring signals occur. Larger measuring signals could be achieved by increasing either the electron current which penetrates the partition or the voltage with which the electrons are accelerated in front of the partition. However, in both cases the energy input into the partition increases and, because the charges which have penetrated are only discharged inefficiently in the wall material (e.g. mica), it brings about a reduction of the life of the apparatus, which can be dramatic, depending on the composition of the wall material.

For this reason there is still the need for an ionization chamber with a non-radioactive source of the type referred to at the beginning and having a sufficient or even higher ionization rate for the required ion molecule reactions in the reaction compartment and, on the other hand, with a stable, vacuum-tight partition with a long service life in operation.

SUMMARY OF THE INVENTION

The problem is solved, on the one hand, by an ionization chamber of the type mentioned at the beginning in which the positive pole of the acceleration section is designed as an x-ray anode in the evacuated compartment, possibly as the surface of the partition, such that a) x-ray light generated in the x-ray anode by impinging electrons reaches the partition in the direction of the reaction compartment, b) the partition is essentially impervious to the electrons of the kinetic energy achieved by the acceleration voltage and largely permeable to the x-ray light generated in the x-ray anode, and c) in the reaction compartment, possibly as the surface of the partition, one or more electrodes are installed in order to generate photoelectrons from the x-ray light passing through the partition.

The problem is also solved by an ionization chamber of the type referred to at the beginning in which the positive pole is designed as an x-ray anode in the evacuated compartment, possibly as the surface of the partition, in such a way that a) x-ray light generated in the x-ray anode reaches the partition in the direction of the reaction compartment, b) the compartment is essentially impervious to electrons of the kinetic energy achieved by the acceleration voltage and is largely permeable to the x-ray light generated in the x-ray anode, c) the x-ray light largely comprises quantum energies below 2 keV, and preferably below 1 keV, when entering the reaction compartment, so that in the reaction compartment air constituents are effectively ionized by the x-ray quanta.

The invention also comprises a method for the ionization of air constituents in a reaction compartment at atmospheric pressure, particularly of an IMS, an ECD, or an APIMS, in which x-radiation is generated by electron bombardment in a vacuum outside the reaction compartment and this x-radiation passes into the reaction compartment through a stable, vacuum tight partition, which is largely transparent for the x-radiation generated, where it releases photoelectrons and/or lower-energy x-ray quanta, which ionize the air constituents, on one or more electrodes.

Finally the invention comprises a method for the ionization of air constituents in a reaction compartment at atmospheric pressure, particularly of an lMS, an ECD, or an APIMS, in which x-radiation is generated by electron bombardment in a vacuum outside the reaction compartment, and this x-radiation passes into the reaction compartment through a stable, vacuum-tight partition which is largely transparent for the x-radiation generated, where the quantum energy of the x-ray quanta is less than 2 keV, and preferably less than 1 keV, so that the x-ray quanta ionize the air constituents with adequate efficiency.

In a preferred embodiment of the ionization chamber according to the invention the partition is made from beryllium and has a thickness of between 10 $\mu$m and 200 $\mu$m. Beryllium windows are essentially known from x-ray equipment and are used due to their good transparency in conjunction with adequate strength. In the preferred thickness range the partition is durable and vacuum tight and represents an impenetrable barrier for electrons. The x-ray light generated in the anode can, on the other hand, pass through the partition virtually unhindered.

A preferred alternative is a partition made from mica with a thickness of between 7 $\mu$m and 40 $\mu$m. Although mica is not as permeable as beryllium for the x-radiation concerned and the partition has to be thinner, the disadvantages of beryllium, i.e. the higher price and toxicity, are avoided.

In embodiments of the invention the acceleration voltage is between 2 keV and 20 keV, and preferably between 5 keV and 15 keV.

In this way x-radiation can be generated in the x-ray anode which is either directly suitable for ionizing air constituents in the reaction compartment or, by conversion in a conversion layer there, releasing photoelectrons and/or generating lower-energy x-radiation which performs this function.

Preferably the x-ray anode contains elements with atomic numbers higher than 50, particularly gold. Consequently a higher level of bremsstrahlung is generated.

The x-ray anode is preferably placed inside the evacuated compartment at a distance from the partition so that essentially none of the electrons emanating from the electron source reach the partition. This is achieved, for example, by an arrangement where the electrons are accelerated toward the x-ray electrode approximately parallel to the partition, where they hit at approx. less than 45° and generate x-radiation (characteristic radiation and bremsstrahlung). Only the x-radiation hits the partition, which is thus not encumbered by electrons.

Alternatively, however, the x-ray anode can be applied to the partition as a metal layer, so the electrons from the electron source which hit the anode are decelerated in the metal layer and generate x-radiation which enters the partition on the opposite side and penetrates it.

The metal layer should preferably be thick enough for it to cover at least 7 half-value layers of the electrons penetrating from the electron source, so that practically no electrons reach the partition direct and the thermal load is already significantly reduced due to the conductivity of the metal layer.

However, on the other hand, the metal layer should be thin enough for it to cover a maximum of two half-value layers of x-radiation generated. This ensures that adequately intense x-radiation penetrates the partition into the reaction compartment.

Preferably the electron source includes a thermionic cathode. This is the most common way of generating electrons. However, the invention can also be used in conjunction with other electron sources.

In one embodiment of the invention the electrode is accommodated in the reaction compartment as a conversion layer on the partition. This is an easily implemented variant. The x-radiation entering through the partition generates in its volume and on its surface, photoelectrons and/or lower energy x-ray quanta which enter the reaction compartment and ionize air constituents there.

The conversion layer should preferably be sufficiently thick for it to cover at least 1 but a maximum of 7 half-value layers of the x-radiation impinging on it. This ensures an adequate level of efficiency for conversion.

In particular the thickness of the conversion layer is between 1 $\mu$m and 200 $\mu$m, depending on the conversion material used, which can also have more than one constituent, and the energy of the x-ray quanta entering. Conversion to lower-energy radiation and ultimately photoelectrons can take place via several conversion stages, whereby the use of adapted materials is recommended accordingly.

Alternatively, the electrode or electrodes in the reaction compartment can also be positioned at a distance from the partition so that x-radiation hits the conversion layer(s) at an angle.

A further development of this embodiment uses several essentially parallel electrodes in the reaction compartment which are positioned at a distance from the partition, such that x-radiation hits the conversion layers at an angle of about 90°. As a result the incident x-radiation in the reaction compartment is very effectively converted into radiation and/or electrons which ionize the air constituents with a good level of efficiency.

The individual electrodes should be sufficiently thick for each of them to cover about one tenth to one half-value thickness of the x-radiation hitting them, so that all the electrodes contribute to conversion.

This effect can be further intensified by enlarging the effective areas of conversion if the one or more electrodes is/are placed in the reaction compartment at a distance from the partition and if they have a louvered surface structure.

In one embodiment the conversion layers are comprised of materials, the K-shell levels of which are smaller than the mean quantum energies of the x-radiation hitting them. Therefore secondary x-radiation, which has a lower quantum energy and is therefore better suited to effective ionization, can be generated, in a cascade if required.

In one embodiment the conversion layers are comprised of materials, the K-shell levels of which are approximately the same as the mean quantum energies of the x-radiation hitting them. Therefore photoelectrons are effectively released which ionize the air constituents.

When using several elements in the conversion layers, the two effects just mentioned can also be combined. Lower-energy x-ray quanta are generated, in several stages if required. They either ionize air constituents with an already good degree of efficiency or they then release photoelectrons which cause the ionization.

Between the electron source and the x-ray anode an additional focusing electrode can be placed which is connected to the acceleration voltage source.

By contrast with a β source, the intensity and/or energy of the electrons, i.e. their range, can advantageously be changed and thereby optimized for the respective conditions, particularly the geometric conditions. In the case of an ECD the electron range can be reduced from about 7 mm for an Ni-63 source to less than 0.2 mm by generating electrons with energy levels of about 1.5 to 2 keV instead of 16 keV for a Ni-63 source, thus considerably reducing the detector volume, for capillary column detectors, for instance, and yet retaining the required, spatially inhomogeneous ionization.

With an IMS the electron range can be adapted to the length of the reaction compartment. This is particularly important in the case of miniaturization (micro-IMS).

By altering the intensity, the sensitivity can be increased or adapted to the respective measurement. If in an upline overview scan or a preceding measurement no product ions are found or only an insufficient quantity, the intensity can be increased correspondingly. Correspondingly, the intensity can be reduced again if the number of product ions is higher than necessary.

Further advantages of the invention are contained in the description and the enclosed drawings. In addition, the above-mentioned, detailed features of the invention can be applied individually or used together in various combinations.

The described embodiments are not to be understood as a conclusive list but, on the contrary, they are examples.

The effects which ultimately lead to the ionization chamber setup according to the invention occurred very surprisingly during experimentation. In the following. there will be a few semi quantitative, more general calculations and estimates in advance, which can provide an initial insight into understanding the background of potential physical mechanisms which are exploited by the invention.

If high-energy electrons penetrate a solid, they are decelerated, whereby their kinetic energy is distributed among new charge carriers (→"Ionization moderation") and the generation of radiation (→"Radiation moderation").

When the primary electron collides with an extranuclear electron of the moderating medium, up to 50% of its kinetic energy is transferred. This energy is distributed over the work function (=bonding energy of the extranuclear electron, e.g. approx. 15 eV for a valence electron or approx. 0.5 . . . 1.5 keV for a K-shell electron) and kinetic energy of the resulting secondary electron. If this energy is sufficiently large, ionization processes can take place again.

Apart from these ionization processes, elastic scattering of the primary and secondary electrons also take place. As kinetic energy declines, the angle of deflection (relative to the original direction of movement) becomes larger and larger. Consequently, and due to the basic non-discriminatability of primary and secondary electrons (the higher-energy one is termed primary electron) the electron paths branch out considerably toward their end, i.e. it is not possible to talk about a defined range of the primary electrons.

If one plots the flux density of monoenergetic electrons relative to the thickness of the moderating medium, there is an almost linear decrease as layer thickness increases, the extrapolated intersection of which with the layer thickness axis is referred to as "mean range". The range is not only stated in x (cm) but also in x ρ (g/cm$^2$) ("Mass range") because as long as the ratio between the atomic number and atomic weight is constant for the moderating medium, the "mass moderating capacity" (−dE/dx)/ρ is virtually independent of the type of medium, i.e. the "linear" ranges x can be converted between the media (e.g. aluminium-copper-air) taking the respective media densities into account.

In some ionization chambers, windows with a thickness of approx. 6 μm and made from muscovite mica (muscovite=potassium mica=KAI$_2$ ((OH$_1$F)$_2$/AI Si$_3$O$_{10}$) mean atomic number: 9.4, mean atomic weight: 19, density: 2.6 . . . 3.2 g/cm$^2$, in the following the calculations use a figure of 2.8, i.e. 6 μm=1.7 mg/cm$^2$) were installed which have an external aluminium thickness (i.e. on the air side) of 30 . . . 50 nm.

The electron range in the window material can be estimated according to the following equation:

$$R = 0.5\ E(1-0.983/(1+4.29\ E)) = \text{approx. 7 } HVT$$

where R is the electron range in g/cm$^2$, E is the electron energy in MeV, and HVT is the half-value thickness, i.e. the layer thickness which halves the energy of the electrons.

The equation was checked by using $^{63}$Ni-β -radiation (mean energy 16 keV) and air as the moderating medium: 1 HVT=0.9 mm air. Other sources in literature state HVT as being 0.5 . . . 1.3 mm air (mean 0.9 mm).

With this equation the electron ranges (in mg/cm$^2$ and in μm mica) and the HVT (in μm mica) were calculated relative to the electron energy:

TABLE 1

| $E_e$ | Range R | | | 6 μm | I/Io after |
|---|---|---|---|---|---|
| [keV] | [mg/cm$^2$] | [μm mica] | HVT | mica = . . . HVT | 6 μm mica |
| 10 | 0.3 | 1.07 | 0.15 | 40.0 | 9.1 × 10$^{-13}$ |
| 15 | 0.6 | 2.14 | 0.31 | 19.4 | 1.4 × 10$^{-6}$ |
| 20 | 0.9 | 3.21 | 0.46 | 13.0 | 1.2 × 10$^{-4}$ |
| 25 | 1.4 | 5.00 | 0.71 | 8.5 | 2.8 × 10$^{-3}$ |
| 30 | 1.9 | 6.79 | 0.97 | 6.2 | 1.4 × 10$^{-2}$ |

Column 5: 6 μm mica corresponds to n HVT

Column 6: Reduction in electron flow after passing through 6 μm mica by a factor of $2^{(number\ of\ HVT)}$.

Below approx. 15 keV and particularly below 10 keV it is highly likely that no primary electrons will pass through the window.

If fast electrons (1 . . . 100 keV) are deflected and decelerated in the Coulomb field of heavy nuclei, the so-called bremsstrahlung occurs, the energy distribution of which ranges from 0 to the maximum energy of the electrons. The intensity peak of the bremsstrahlung spectrum is 1.5 . . . 2 times the short-wave limit, i.e. approx. 10 keV (=1.25 Angstroem) for example if the electrons penetrate the moderating medium at 15 keV ($\lambda^{min}$=0.83 Angstroem). If the electron energy is larger than the energy of the K-, L-, N- . . . shells of the moderating medium, the continuous bremsstrahlung spectrum is superimposed with the discrete lines of the moderating medium, e.g. in the case of muscovite mica: 3.3 keV from the K, 1.5 keV from the Al, and 1.7 keV from the Si; the radiation with 678 eV from F and 517 eV from 0 (52% of the atoms in mica are 0-atoms!) will probably not be able to leave the window because it has to little energy (radiation absorption ~1/energy).

For the yield of bremsstrahlung various authors quote empirical formulas/characteristics from which the following figures are derived for 15 keV electrons for example:

TABLE 2

| Moderating material | Air | Al | Copper | Lead | Mica |
|---|---|---|---|---|---|
| Atomic number | 7.2 | 13 | 29 | 82 | 9.4 |
| Yield | $1.5 \times 10^{-4}$ | $3.3 \times 10^{-4}$ | $10^{-4}$ | $4.2 \times 10^{-4}$ | $2.2 \times 10^{-4}$ |

The bremsstrahlung yields are minimal. Most of the energy of the primary ions is converted to charge carriers (i.e. to secondary electrons) by means of "ionization moderation" and is lost if these secondary electrons do not have adequate energy to leave the window. From Tab. 2 it can be seen that the bremsstrahlung yield could be increased by about 18 times if the primary electrons were not decelerated in the mica (mean atomic number 9.4) but in gold (atomic number 79).

The bremsstrahlung resulting in the window is attenuated on its journey through the window. This reduction in intensity is described by Lambert-Beer' law: $I/I_o = e - (\mu/\rho) x \rho$ with $(\mu/\rho)$=mass attenuation coefficient and $x\rho$=area density of the attenuating layer (up to 1.7 mg/cm² for the mica window). The values for mass attenuation coefficient are summarized in various literature in the form of characteristics and tables. Reductions in the intensity of bremsstrahlung depending on the energy of the primary ions (=maximum energy of the quanta) have been calculated (Tab. 3). 13 and 6.5 keV are the peaks on the bremsstrahlung spectra, which are caused by 20 and 10 keV electrons respectively.

TABLE 3

| Ex [keV] | 20 | 13 | 10 | 6.5 | 3 | 1 |
|---|---|---|---|---|---|---|
| $\mu/\rho$ [cm²/g] | 2.9 | 13 | 26 | 130 | 1,450 | $4.23 \times 10^{-4}$ |
| $(\mu/\rho) \times \rho$ | 0.0046 | 0.022 | 0.044 | 0.221 | 2.465 | 71.825 |
| $I/I_o$ | 0.995 | 0.978 | 0.957 | 0.802 | 0.085 | $6.4 \times 10^{-32}$ |
| $(I/I_o)$ [%] | 0.5 | 2.2 | 4.3 | 19.8 | 91.5 | 100 |

From these calculations it is evident that, as already supposed, radiation with less than 1 keV will not be able to leave the window and the characteristic radiation of K, Al, and Si leaves the window but only highly attenuated. Consequently, the spectrum will be limited to the bremsstrahlung "mountain", i.e. to the energy range from approx. 3 keV ... $E_{max}$.

Attenuation of bremsstrahlung in the exterior aluminium layer, which is 30 ... 50 nm thick, is minimal, as indicated by the figures in Tab. 4. An average thickness of 40 nm=$4 \times 10^{-6}$ cm is assumed, which, multiplied by the density of the aluminium (=2.7 g/cm²), is equivalent to a mass layer thickness of $1.1 \times 10^{-5}$ g/cm².

TABLE 4

| Ex [keV] | 3 | 6.5 | 10 | 13 | 20 |
|---|---|---|---|---|---|
| $\mu/\rho$ [cm²/g] | 1,450 | 130 | 26 | 13 | 2.9 |
| $(\mu/\rho) \times \rho$ | 0.016 | 0.0014 | $2.9 \times 10^{-4}$ | →0 | →0 |
| $I/I_o$ | 0.984 | 0.999 | 0.9997 | →1 | →1 |
| $(I/I_o)$ [%] | 1.6 | 0.1 | 0.03 | →0 | →0 |

The loss in the intensity of the bremsstrahlung in the window is due to interaction between the quanta and the shell electrons of the atoms of the window materials. At low atomic numbers and low quantum energies that is the photo effect.

The photo effect is a pure absorption process. The entire quantum energy $E_x$ is transferred to an electron which then leaves the atom with a kinetic energy of $E_{kin}=E_x-E_i$, where $E_i$ refers to the bonding energy of the electron in its shell (K, L, M, ... ). If the quantum energy is larger than E (K) (=bonding energy in the K-shell), photo absorption chiefly takes place (approx. 80%) in the K-shell and only about 20% takes place in higher shells. The probability of the photo effect is highest if the quantum energy is just a little higher than the bonding energy of the electron. The emission angle of the photoelectron (relative to the direction of incidence of the quantum) is dependent on the quantum energy: 11° at 11.3 MeV, 43° at 79 keV, 65° at 17 keV, and →90° at even smaller energies.

If the kinetic energy passed on to the photoelectron is larger than the bonding energy of electrons in adjacent atoms, secondary electrons will be released there.

The hole which the photoelectron leaves behind (e.g. in the K-shell) is filled by a more distant electron which, with its jump, releases the path energy differential through radiation. This characteristic x-radiation can again liberate a photoelectron in an adjacent atom (naturally with less energy). However, the so-called intrinsic photoeffect is also possible, in which—without any radiation—a further (more distant) extranuclear electron of the same atom is emitted (Auger effect): an L-electron fills the hole in the K-shell and passes the energy differential on to the other L-electron, for example, which can consequently leave the atom, whereby the energy imparted is approximately E(K)−2E(L) (for aluminium for example : approx. 1,500 eV−2×165 eV=1.2 keV). Such radiation-free transitions are very probable with light elements.

The process of "filling holes" can be continued in a cascade so that a large number of electrons are released which have a wide range of low energies.

The described interaction processes can take place both in the window material and in the air in the IMS ion source.

Feasible methods are described which can lead to saturation currents in the IMS ion source.

The electrons produced and accelerated in the ion source penetrate the window and create bremsstrahlung with a power of $1.2 \times 10^{14}$ eV/s (as described in the previous chapters). According to the empirical equation $P=1.5 \times 10^{-9} \times Z \times i \times U^2$, whereby P is the bremsstrahlung power at complete absorption of the electron beam, Z is the atomic number of the moderating medium, i is the electron flow, and U is the voltage to accelerate the electrons, this power can be estimated at $8.8 \times 10^{13}$ eV/s (the condition "complete absorption of the electron beam" can, as was shown, be regarded as fulfilled), the deviation is about −25%. The radiation spreads in a $4\pi$ geometry; we are only concerned with the hemisphere directed toward the IMS ion source (→factor 0.5). The bremsstrahlung spectrum probably has an intensity peak at approx. 6.5 keV—so this value is used in the further calculation (→factor 0.65). About 20% of the radiation is attenuated in the window (→factor 0.8). In the thin aluminium layer on the outer window surface 0.1% of the radiation is absorbed and converted into photoelectrons. The aluminium electrons are (on average) bound at 170 eV. Consequently, approx. $1.8 \times 10^8$ photoelectrons result per second, of which only the 50% which leave the aluminium layer toward the IMS ion source (→factor 0.5) are important. The mean energy of these photoelectrons can only be estimated with difficulty. If it is about 1 keV (or slightly more) (e.g. L-shell Auger electrons, see above), these electrons have a chance of leaving the aluminium layer: an average aluminium layer thickness of 40 nm corresponds to 6.8 HVT for 1 keV electrons, i.e. the probability that these electrons leave the window is 1%. A 1 keV electron produces about 3 ion pairs per cm and Torr in air; at 760 Torr and a maximum range of 120 μm (=10 HVT) this produces 27.4 ion pairs per photoelectron or $2.5 \times 10^9$ ion pairs per second. If one multiplies this figure by the elementary charge, the saturation current will be about 410 pA. On the other hand, the energy input of $9 \times 10^7$ electrons/s×1 keV/electron into the air of the IMS ion source can also be used to calculate the saturation current by dividing it by the air-specific ionization effort of approx. 34 eV per ion pair and then multiplying it by the elementary charge: 420 pA.

The measured saturation currents are between 170 and 330 pA (depending on the electron source).

As an alternative to the way described here, it is also plausible that the air ionization occurs not via the intermediate step "photoelectrons from the aluminum layer", but rather directly via the interaction of the bremsstrahlung quanta with the nitrogen and oxygen atoms in the air. In the first step, the form of interaction is the photo effect on the atoms with the formation of photoelectrons, while in the second step it is the ionization of the $N_2$ and $O_2$ molecules by these photoelectrons. Since the quanta are not charged, they have only a low probability of interaction, i.e. the bremsstrahlung quanta (compared with electrons of the same energy) have ranges about 1,500 times greater in air.

In Table 5 the radiation ranges R (1%) are listed with the distances required to reduce radiation to <1% (line 3), as well as the values for reduction of radiation in the reaction compartment (approx. 3 cm long, line 4), and reduction of radiation in the whole IMS measuring cell (approx. 8 cm long, line 5).

If the quanta have energies greater than 3 keV, as estimated above, they should travel through the whole measuring cell with only minimal interaction and impinge on the collecting electrode. This would result in a constant ionization current (caused by the ionization in the drift compartment and by release of photoelectrons in the collecting electrode), which causes an increase in the baseline of the spectrum. However, since this was not observed, one has to conclude that either the quanta do not reach the drift compartment, or that their probability of interaction in the IMS measuring cell is so low that they cause almost no detectable effects. In order to estimate the proportion of radiation which enters the IMS measuring cell (more specifically, the reaction compartment), the ratio of the reaction compartment volume (approx. 2.5 $cm^3$) to the volume of a sphere with a radius R (1%) is introduced as a correction factor.

Table 6 shows the results (ion pairs as well as saturation current) in consideration of the geometric proportions.

TABLE 6

| Ex [keV] | 1 | 1.5 | 2 | 3 | 6.3 |
|---|---|---|---|---|---|
| R (1%) [cm air] | 1.2 | 3.5 | 6.7 | 24 | 178 |
| Correction factor for the proportion of absorption in the reaction compartment | 0.13 | 0.014 | 0.002 | $4.3 \times 10^5$ | $1.04 \times 10^7$ |
| Ion pair(s) in the reaction compartment | $1.2 \times 10^{-11}$ | $1.3 \times 10^{-10}$ | $1.8 \times 10^{-9}$ | $3.8 \times 10^{-7}$ | $9.4 \times 10^{-4}$ |
| Saturation current | 19 nA | 2.1 nA | 290 pA | 6.2 pA | 15 fA |

From the values in the last line of table 6 one can see that two effects can come into play. If the bremsstrahlung spectrum spans the energy range of approx. 3 keV up to the energy of the primary electrons, air ionization by the bremsstrahlung is hardly probable; if, however, the lower energy component in the spectrum is not to be neglected, then the ionization current caused by the bremsstrahlung can quickly begin to dominate.

The invention is depicted in the diagrams and explained and described using actual embodiments in more detail.

BRIEF DESCRIPTION OF THE DRAWING

FIG. 1: Scheme of a known IMS spectrometer;

FIG. 2: Source of the bremsstrahlung, which forms the evacuated compartment of an ionization chamber according to the invention;

| Ex [keV] | 1 | 1.5 | 2 | 3 | 5 | 6.5 | 10 | 13 | 15 | 20 |
|---|---|---|---|---|---|---|---|---|---|---|
| μ/ρ [$cm^2$/g] in air | 3000 | 1000 | 530 | 150 | 38 | 20 | 6.2 | 2.5 | 1.5 | 0.9 |
| R (1%) [cm] | 1.2 | 3.5 | 6.7 | 24 | 93 | 178 | 572 | 1418 | 2364 | 3940 |
| Reduction of . . . % in reaction compartment | 100 | 98 | 87.3 | 44.3 | 13.8 | 7.5 | 2.4 | 1 | 0.6 | 0.4 |
| in measuring cell | 100 | 100 | 99.5 | 77.7 | 31.6 | 18.1 | 6.2 | 2.5 | 1.5 | 0.9 |

Figure 3A:
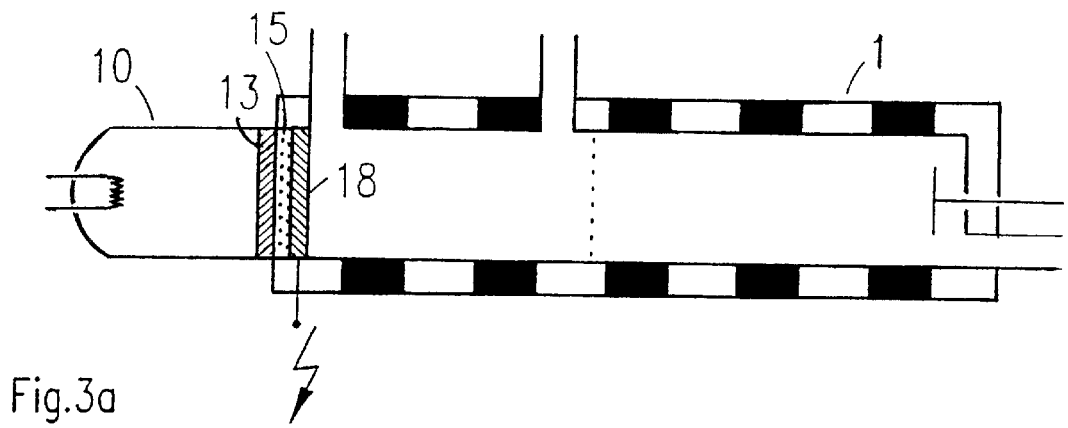
FIG. 3a: Axial arrangement of the bremsstrahlung source (10) and the IMS measuring cell (1); the conversion layer (18) is parallel to and in front of the window (18)
Figure 3B:
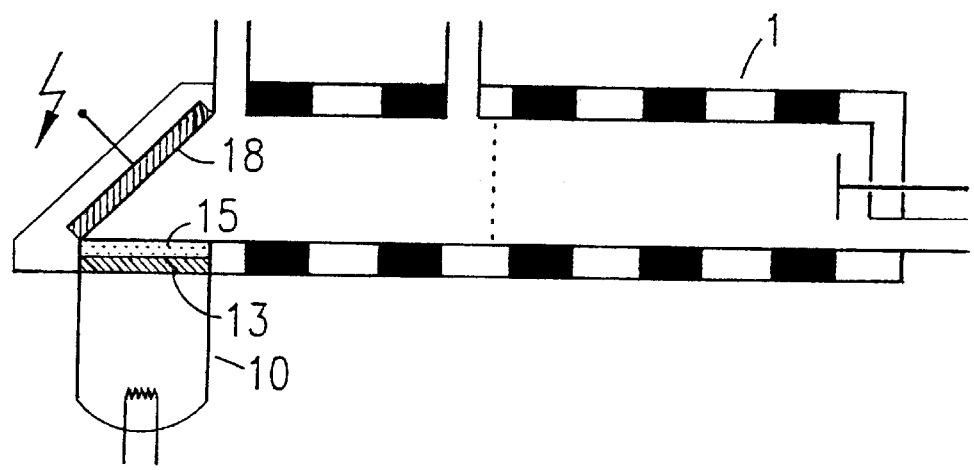
Figure 3C:
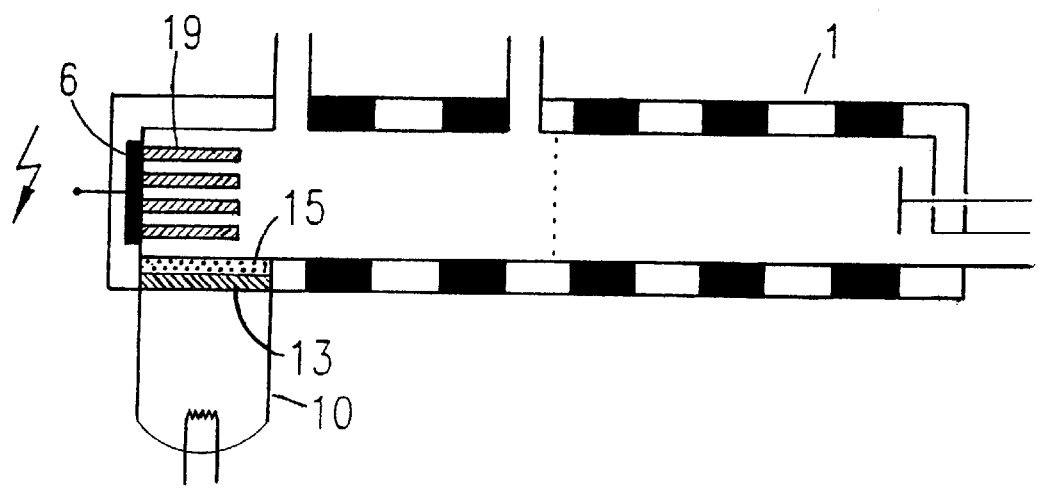

FIG. 3b: The radiation source (10) emits its quanta mainly perpendicular to the axis of the IMS measuring cell (1); the conversion layer (18) is fixed at an angle of 45° to the axis;

FIG. 3c: Arrangement of the radiation source (10) and the IMS measuring cell (1) as in FIG. 3b; the conversion layer (18) consists of a multitude of parallel louvers (19) which are aligned along the axis of the IMS measuring cell.

DESCRIPTION OF THE PREFERRED EMBODIMENTS

In the following, embodiments are now discussed with reference to the figures.

In FIG. 1, a conventional IMS measuring cell (1) with an ionization chamber is schematically represented.

The measuring cell (1) consists of a drift compartment (2), the ion admission grid (3), the reaction compartment (4) and a front area (5) with a repulsion electrode (6).

The drift compartment (2) has, for example, a diameter of 1 or 2 cm and a length of between 5 and 10 cm. Discrete or continuous structures such as field support rings or homogenous resistance coatings serve to maintain an electrical field with a strength of between 200 and 300 V/cm along the axis of the cylindrical drift compartment (2).

At the gas inlet (7), clean, dry air enters the drift compartment at a flow-rate of between 5 and 20 I/h. The ion admission grid (3) is located between the drift compartment (2) and the reaction compartment (4); the grid can (for example) be one of a Nielsen-Bradbury type. The diameter of the reaction compartment (4) can be exactly as big as or smaller than that of the drift compartment (2), its length being, for example, between 1 and 3 cm. Field support structures analogous to those of the drift compartment maintain the electrical field at a strength of 200–300 V/cm along the axis of the chamber. The reaction compartment (4) is perfused with clean, dry air at a flow-rate of 5 to 20 liters per hour from the inlet (8) to the outlet (9), the latter of which also serves as the outlet for the drift gas.

At the front end (5) of the reaction compartment (4) the ion source is usually located, which is normally a Ni-63 β-radiation source, or a corona needle, or a vacuum UV lamp (e.g. 10.6 eV and 117 nm).

The repulsion electrode (6) is arranged between the front area (5) and the gas inlet (8) and lies at the maximum point of the potential difference along the axis of the IMS measuring cell (1), and which as a result repels the charge carriers formed in area (5) into the reaction compartment.

A bremsstrahlung source (10) is represented in FIG. 2.

The bremsstrahlung source (10) consists of an evacuated container (11) (pressure $<10^6$ Torr), made, for example, of glass, in which a directly or indirectly heated thermionic cathode (12) and an anode (13) constructed from a preferably heavy metal, e.g. gold, is located. Both electrodes are connected to the voltage source (14), which provides the potential difference for accelerating the electrons (e.g. 10–15 kV). The width of the anode (13) has to be such that the accelerated electrons are extensively absorbed within it; for gold this amounts to several hundreds of nanometers.

Behind the anode (13) there is a window (15), which is hermetically sealed to the wall of the container (11), for example, by gluing. The anode (13) can be connected to the window (15) or it can be arranged so that it is mechanically separated from the window (15). The window (15) is impermeable to air, although for the bremsstrahlung it is largely transparent, and it must be thick enough to withstand the pressure difference.

Examples of appropriate window materials include beryllium (25–100 μm thick) or mica (5–10 μm thick).

The electrons emitted from the thermionic cathode (12) are accelerated in the direction of the anode (13) to between 10 and 15 keV and penetrate into the anode material, whereby bremsstrahlung arises which escapes from the anode (13). The anode (13) is as thick as is required so that the main proportion of the electrons impinging on it can not pass through it, but the bremsstrahlung can leave the anode (13) only slightly weakened. An appropriate width is approx. 0.4 μm, corresponding to 10 half-life thicknesses for 15 keV electrons in gold (it reduces the electron current to about 0.1%) and weakens the radiation produced by less than approx. 10%.

In order to keep absorption losses of the radiation to a minimum in the window (15), a material with a low atomic number is chosen (e.g. beryllium with an atomic number of 4, or muscovite mica with an average atomic number of 9.4).

If the energy of the bremsstrahlung quanta is lower than 2 keV, the air can be effectively ionized in area 5 of FIG. 1. If it is larger than 2 or 3 keV, its conversion to photoelectrons is required. For this purpose, an appropriate metal, e.g. aluminum, is exposed to the radiation.

FIGS. 3a, b and c show various arrangements and embodiments of this conversion layer (18) between the bremsstrahlung source (10) and the IMS measuring cell (1).

The axial arrangement of the bremsstrahlung source (10) and the IMS measuring cell (1) is represented in FIG. 3a. The conversion layer (18) is found both upon and in front of the window (15), and is bonded to the window (15), e.g. vapor-deposited or layered on. The thickness of the layer (18) is between 1 and 7 half-life thicknesses of aluminum for photoelectrons, e.g. 50–350 nm for 5 keV electrons. In the layer (18), less than 1% of the bremsstrahlung output is converted into photoelectrons. If the layer (18) was chosen to be thicker, more radiation would be converted into photoelectrons, but the electrons arising would be of too low an energy to leave the layer (18). The layer (18) is at the high voltage potential of the IMS measuring cell (1) and functions simultaneously as a repulsion electrode (6) for the reactant ions produced by the photoelectrons.

FIG. 3b shows an embodiment whereby the radiation enters laterally into the IMS measuring cell and impinges upon the conversion layer (18) inclined at 450° to the axis of the IMS measurement cell (1). The distance from the window (15) of the radiation source to the layer (18) corresponds to the diameter of the reaction compartment (4) of the IMS measuring cell (1). The thickness of the layer (18) can amount to 1 mm or more; conversion of the bremstrahlung into photoelectrons occurs primarily in the first 350–400 nm of the layer (18). The layer (18) is once again at the high voltage potential of the IMS measuring cell (1) and in this way forces the formed reactant ions into the reaction compartment (4) of the IMS measuring cell (1).

A third embodiment is given in FIG. 3c. The formation of photoelectrons occurs in and on a multitude of aluminum louvers (19), which are fixed in an electrically conducting manner on the repulsion electrode (6) of the IMS measuring cell (1) parallel to the axis of the measuring cell, and which are irradiated by the bremsstrahlung entering the measuring cell (1) from the side. The length of the louvers (19) can be between a few micrometers and a few millimeters, as can their distance from one another. The louvers (19) do not have to be disc-shaped, but can also be rod-like or spherical. They cover the repulsion electrode (6) over its entire surface and are distributed in a regular or irregular fashion. In this way, the conversion layer (18) acquires a large surface area from which more photoelectrons can appear than can appear from other embodiments. In extreme cases, the conversion layer could be distributed in a sponge-like fashion.

The claimed invention is:

1. An ionization chamber with a non-radioactive ionization source comprising an evacuated compartment and a reaction compartment, into which an analyte may be introduced and discharged, the reaction compartment being separated from the evacuated compartment by a gas-impermeable partition, and a non-radioactive electron source being located in the evacuated compartment and forming a negative pole of an acceleration path, wherein a positive pole of the acceleration path is formed as an x-ray anode located in the evacuated compartment and a) x-ray light produced in the x-ray anode by impinging electrons reaches the partition, b) the partition is substantially impermeable to said impinging electrons but substantially permeable to the x-ray light produced in the x-ray anode, and c) in the reaction compartment at least one electrode is arranged for producing photoelectrons in response to x-ray light having passed through the partition.

2. The ionization chamber of claim 1, wherein the partition comprises of beryllium and has a thickness of between 10 $\mu$m and 200 $\mu$m.

3. The ionization chamber of claim 2, wherein an acceleration voltage applied to the ionization chamber is between 2 keV and 20 keV.

4. The ionization chamber of claim 1, wherein the partition comprises of mica and has a thickness of between 7 $\mu$m and 40 $\mu$m.

5. The ionization chamber of claim 4, wherein an acceleration voltage applied to the ionization chamber is between 2 keV and 20 keV.

6. The ionization chamber of claim 1, wherein the x-ray anode is applied to the partition as a metal layer, whereby impinging electrons from the electron source are decelerated in the metal layer and produce x-rays which enter the partition on the opposite side of the metal layer.

7. The ionization chamber of claim 6, wherein the metal layer has a flat profile along a predominant plane, and a thickness perpendicular to said plane that is at least 7 half-value thicknesses of the electrons penetrating the metal layer from its side facing the electron source.

8. The ionization chamber of claim 7, wherein the metal layer has a flat profile along a predominant plane, and a thickness perpendicular to said plane that is less than 2 half-value thicknesses of the x-rays produced in the metal layer.

9. The ionization chamber of claim 1, wherein the electrode is installed within the reaction compartment in the form of a conversion layer on the partition.

10. The ionization chamber of claim 9, wherein the conversion layer has a flat profile along a predominant plane, and a thickness perpendicular to said plane that is between 1 and 7 half-value thicknesses of the x-ray radiation impinging upon it.

11. The ionization chamber of claim 10, wherein the thickness of the conversion layer is between 1 $\mu$m and 200 $\mu$m.

12. The ionization chamber of claim 1, wherein at least one electrode in the reaction compartment is arranged such that the x-ray radiation impinges on it at an angle.

13. The ionization chamber of claim 1, wherein a plurality of substantially parallel electrodes are arranged in the reaction compartment such that the x-ray energy impinges upon the electrodes at an angle of about 90°.

14. The ionization chamber of claim 13, wherein the individual electrodes are thick enough so that their individual thicknesses are between a tenth and one half-value thickness for the impinging x-ray radiation.

15. The ionization chamber of claim 1, wherein at least one electrode in the reaction compartment has a louvered surface structure.

16. The ionization chamber of claim 1, wherein the electrode has a conversion layer comprising a material for which K-shell levels are smaller than the average quantum energies of the x-rays impinging upon them.

17. The ionization chamber of claim 1 wherein the electrode has a conversion layer comprising a material for which K-shell levels overlap with the average quantum energies of the x-rays impinging upon them.

18. An ionization chamber with a non-radioactive ionization source comprising an evacuated compartment and a reaction compartment into which an analyte may be introduced and discharged, the reaction compartment being separated from the evacuated compartment by a gas impermeable partition, and a non-radioactive electron source being located in the evacuated compartment and forming a negative pole of an acceleration path, wherein a positive pole is formed as an x-ray anode located in the evacuated compartment and a) x-ray light produced in the x-ray anode by impinging electrons reaches the partition, and b) the partition is substantially impermeable to said impinging electrons but substantially permeable to the x-ray light produced in the x-ray anode, such that the x-ray light entering the reaction compartment has primarily quantum energies under 2 keV, and the analyte substance in the reaction compartment is ionized by x-ray quanta of the x-ray light.

19. The ionization chamber of claim 18, wherein the partition comprises beryllium and has a thickness of between 10 $\mu$m and 200 $\mu$m.

20. The ionization chamber of claim 19, wherein an acceleration voltage applied to the ionization chamber is between 2 keV and 20 keV.

21. The ionization chamber of claim 18, wherein the partition comprises of mica and has a thickness of between 7 $\mu$m and 40 $\mu$m.

22. The ionization chamber of claim 21, wherein an acceleration voltage applied to the ionization chamber is between 2 keV and 20 keV.

23. A method for ionizing an analyte substance in a reaction compartment comprising producing x-ray energy in an evacuated compartment by electron bombardment, the evacuated compartment being separated from the reaction compartment by a partition that is at least partially transparent to the x-ray energy but substantially impermeable to the electrons used in said bombardment, wherein an electrode in the reaction compartment releases photoelectrons in response to the x-ray energy, the photoelectrons ionizing the analyte substance.

24. A method for ionizing an analyte substance in a reaction compartment comprising producing x-ray quanta outside the reaction compartment by electron bombardment within a vacuum and directing the x-ray quanta through a partition that is substantially gas-impermeable, but at least partially transparent to the x-ray energy, wherein the quantum energy of the x-ray quanta is below 2 keV.

25. An ionization apparatus comprising:

a source compartment containing an x-ray source that emits x-ray energy;

a reaction compartment containing an analyte substance to be ionized; and a partition between the source compartment and the reaction compartment that is substantially impermeable to gas and at least partially transparent to the x-ray energy, such that the x-ray energy passes through the partition from the source compartment to the reaction chamber, resulting in the ionization of the analyte substance.

26. An ionization apparatus according to claim 25 wherein the x-ray source comprises a non-radioactive electron source that emits electrons and an x-ray anode that emits the x-ray energy in response to the electron source electrons being incident upon it.

27. An ionization apparatus according to claim 25 wherein the analyte substance is ionized directly by the x-ray energy.

28. An ionization apparatus according to claim 25 wherein the reaction chamber further comprises a photoelectron source that emits electrons in response to x-ray energy incident upon it, and the electrons from the photoelectron source ionize the analyte substance.

29. An ionization apparatus according to claim 28 wherein the photoelectron source comprises a conversion layer adjacent to the partition.

30. An ionization apparatus according to claim 29 wherein the conversion layer has a flat profile and resides along a plane that is at an angle relative to a plane perpendicular to a primary direction of the x-ray energy.

31. An ionization apparatus according to claim 29 wherein the conversion layer comprises a plurality of parallel louvers.

32. An ionization apparatus according to claim 25 wherein the reaction chamber is at approximately atmospheric pressure.

33. An ionization apparatus according to claim 25 wherein the source compartment is at a vacuum.

34. An ionization apparatus according to claim 25 wherein a majority of the x-ray energy has quantum energies below 2 KeV.

35. An ionization apparatus according to claim 25 wherein the partition comprises beryllium.

36. An ionization apparatus according to claim 35 wherein the partition has a thickness of between 10 $\mu$m and 200 $\mu$m.

37. An ionization apparatus according to claim 25 wherein the partition comprises mica.

38. An ionization apparatus according to claim 37 wherein the partition has a thickness of between 7 $\mu$m and 40 $\mu$m.

39. A method of ionizing an analyte substance, the method comprising:

providing a source compartment containing an x-ray source that emits x-ray energy;

locating the analyte substance in a reaction compartment adjacent to the source compartment; and separating the source compartment and the reaction compartment with a partition that is substantially impermeable to gas and at least partially transparent to the x-ray energy, such that the x-ray energy passes through the partition from the sources compartment to the reaction chamber, resulting in the ionization of the analyte substance.

40. A method according to claim 39 wherein the x-ray source comprises a non-radioactive electron source that emits electrons and an x-ray anode that emits the x-ray energy in response to the electron source electrons being incident upon it.

41. A method according to claim 39 wherein the analyte substance is ionized directly by the x-ray energy.

42. A method according to claim 39 wherein the reaction chamber further comprises a photoelectron source that emits electrons in response to x-ray energy incident upon it, and the electrons from the photoelectron source ionize the analyte substance.

43. A method according to claim 42 wherein the photoelectron source comprises a conversion layer adjacent to the partition.

* * * * *